US006225046B1

(12) United States Patent
Vesey et al.

(10) Patent No.: US 6,225,046 B1
(45) Date of Patent: May 1, 2001

(54) METHOD FOR DETECTING MICROORGANISMS

(75) Inventors: Graham Vesey, Drummoyne; Duncan Veal, Turramurra; Keith Williams, Frenchs Forest, all of (AU)

(73) Assignees: Macquarie Research Ltd.; Australian Water Technologies Pty Ltd., both of New South Wales (AU)

( * ) Notice: Subject to any disclaimer, the term of this patent is extended or adjusted under 35 U.S.C. 154(b) by 0 days.

(21) Appl. No.: 08/942,206

(22) PCT Filed: Apr. 3, 1996

(86) PCT No.: PCT/AU96/00192

§ 371 Date: Jul. 28, 1998

§ 102(e) Date: Jul. 28, 1998

(87) PCT Pub. No.: WO96/31777

PCT Pub. Date: Oct. 10, 1996

(30) Foreign Application Priority Data

Apr. 3, 1995 (AU) .................................................. PN2140

(51) Int. Cl.⁷ ........................ G01N 11/02; G01N 33/533; C07K 14/005; C07K 14/195
(52) U.S. Cl. .................................. 435/5; 435/4; 435/7.1; 435/7.2; 435/239; 436/63; 436/518; 436/546
(58) Field of Search ............................ 435/5, 7.1, 4, 239, 435/7.2; 436/546; 530/388.1, 388.3

(56) References Cited

U.S. PATENT DOCUMENTS

| 4,421,860 | 12/1983 | Elings et al. ............................ 436/518 |
| 4,581,334 | 4/1986 | Kirchanski et al. ..................... 435/29 |
| 4,665,020 | 5/1987 | Saunders .................................... 435/7 |
| 4,780,423 | 10/1988 | Bluestein et al. ..................... 436/527 |
| 5,290,707 | 3/1994 | Wood ..................................... 436/523 |
| 5,326,692 | 7/1994 | Brinkley et al. ......................... 435/6 |
| 5,380,663 | * 1/1995 | Schwartz et al. . |
| 5,552,290 | * 9/1996 | Michelson et al. . |
| 5,567,627 | * 10/1996 | Lehnen . |
| 5,627,037 | * 5/1997 | Ward et al. . |
| 5,627,040 | * 5/1997 | Bierre et al. . |
| 5,629,147 | * 5/1997 | Asgari et al. . |
| 5,776,711 | * 7/1998 | Vyas et al. . |
| 5,814,468 | * 9/1998 | Siiman et al. . |
| 5,948,627 | * 9/1999 | Lee et al. . |

FOREIGN PATENT DOCUMENTS

| 0 063 852 A2 | 3/1982 | (EP) . |
| 0 124 050 A1 | 7/1984 | (EP) . |
| 0121442 | 10/1984 | (EP) . |
| 0 149 565 A2 | 7/1985 | (EP) . |
| 0 201 211 A1 | 12/1986 | (EP) . |
| 0 216 191 A1 | 4/1987 | (EP) . |
| 0 296 136 A1 | 12/1988 | (EP) . |
| 0 536 593 A1 | 4/1993 | (EP) . |
| 0 595 641 A2 | 5/1994 | (EP) . |
| 2 095 831 | 10/1982 | (GB) . |
| 6 1132-869 | 6/1986 | (JP) . |
| 6 3095-357 | 4/1988 | (JP) . |
| 0 2151-766 | 6/1990 | (JP) . |
| 0 2195-257 | 8/1990 | (JP) . |
| 05107249 | 4/1993 | (JP) . |
| 05281230 | 10/1993 | (JP) . |
| 05312811 | 11/1993 | (JP) . |
| 06027112 | 2/1994 | (JP) . |
| 06094716 | 4/1994 | (JP) . |
| 06130063 | 5/1994 | (JP) . |
| 06160387 | 6/1994 | (JP) . |
| WO 84/04169 | 10/1984 | (WO) . |
| WO 86/04684 | 8/1986 | (WO) . |
| WO 86/06493 | 11/1986 | (WO) . |
| 93-18068 | 9/1993 | (WO) . |

OTHER PUBLICATIONS

Derek Craston and John Francis, "Selective Particle Counting by Means of Affinity Ligands Linked to Microscopically Visible Labels," *Analytical Proceedings*, Jun. 1993, vol. 253–255.

Jomar Frengen, et al., "Dual Analyte Assay Based on Particle Types of Different Size Measured by Flow Cytometry," *Journal of Immunological Methods*, 178 (1995) 141–151.

Graham Vesey et al, "Detection of Specific Microorganisms in Environmental Samples Using Flow Cytometry," *Methods in Cell Biology*, vol. 42, 1994, 490–522.

Diaper & Edwards, The use of Fluorogenic esters to detect viable bacteria by flow cytometry, *J. Appl. Bacteriol.* (1994) 77:221–228.

Faber et al., Cyroperservation of fluorescent marker –labeled Algae (Selenastrum capricornutum) for toxicity testing using flow cytometry, *Environ. Toxicol. Chem.* (1997) 16:1059–1067.

\* cited by examiner

*Primary Examiner*—Phuong T. Bui
(74) *Attorney, Agent, or Firm*—Morgan, Lewis & Bockius LLP

(57) ABSTRACT

Methods for detecting microorganisms in a sample by binding detectable particles and fluorescent labelled ligands reactive to the microorganisms. The present invention also includes the use of multiple fluorochromes for the detection of microorganisms and is adaptable for use in flow cytometry.

14 Claims, 2 Drawing Sheets

METHOD FOR DETECTING MICROORGANISMS

TECHNICAL FIELD

The present invention relates to methods for detecting the presence of microorganisms in a sample rising particles bearing a ligand reactive to the microorganisms and fluorescent labelled ligands. The methods are suitable for flow cytometric detection of microorganisms.

BACKGROUND ART

Testing samples for the presence of microorganisms. in particular human pathogens. is an important part of monitoring samples including biological samples, foods, drinks, the environment and water supplies. In order to obtain immediate results testing often involves the direct analysis of samples for specific microorganisms. This can be labour intensive and routine for the technician involved. In particular. there is an increasing need to monitor water supplies to ensure they meet strict standards for human consumption. This often involves the testing of large volumes of water in order to detect relevant numbers of microbial contaminants which is time consuming and expensive. Automated methods and apparatus are being developed to assist in the large scale testing of samples for microbial contamination. The methods presently in use are often insensitive and do not allow the identification of specific microorganisms present in the samples being tested.

Flow cytometric detection of specific microorganisms relies on labelling the target organism with highly specific probes attached to fluorochrome molecules. To enable accurate detection. two or more different fluorescent labels need to be attached to the target organism (Vesey et al. 1994A). The types of probes available for these techniques are monoclonal and polyclonal antibodies, lectins and oligonucleotides. The range of fltiorochromes that can be coupled to these probes is limited. For example, many flow cytometers utilise a 488 nm laser to illuminate the sample, and accordingly, the choice of fluorochromes is limited to those which can be excited at 488 nm for those machines.

For a flow cytometer to distinguish one fluorochrome from another, the fluorochromes must emit at different wavelengths. There are only three types of fluorochromes presently available that excite at 488 nm and emit at wavelengths different enough to be distinguished by flow cytometry: green fluorochromes such as fluorescein isothiocyanate (FITC); red fluorochromes such as phycoerythrin (PE) and tandem fluorochromes. Unfortunately, the tandem fluorochromes are often not bright enough to be used in many applications. Therefore, flow cytometry is often limited to the detection of two fluorochromes. In applications such as the detection of specific microorganisms in a range of sample types, this poses a problem if there are only a small number of sites available for recognition on the microorganism. The level of sensitivity that can be achieved with two fluorochromes is often not good enough for these applications.

The present inventors have developed methods of detecting microorganisms in a fluid sample utilising particles and fluorescent labelled ligands reactive to microorganisms.

DISCLOSURE OF THE INVENTION

Accordingly. the present invention consists in a method of detecting the presence of microorganisms of a predetermined type in a sample containing the microorganisms. the method comprising the steps of:

(a) treating the sample with at least one detectable particle, each particle bearing a ligand reactive to the microorganisms of the predetermined type, the sample being treated for a period of time sufficient to allow the microorganisnms of the predetermined type in the sample to bind to the particle via the ligand;

(b) further treating the sample with at least one ligand labelled with a fluorescent marker, the ligand being reactive to the microorganisms of the predetermined type, the sample being treated for a period of time sufficient to allow the at least one ligand to bind to the microorganisms of the predetermined type; and (c) analysing the sample so as to detect the presence of a particle associated with one or more of the fluorescent markers, the ligands being so selected that such an association is indicative of the presence of microorganisms of the predetermined type in the sample.

In a preferred embodiment of the present invention the particle is a fluorescent particle and more preferably a fluorescent latex bead. The beads preferably have a nominal diameter from 10 nanometres to 0.1 millimetres. The beads are preferably detectable by virtue of being fluorescently labelled. More than one type of particle can be used with each type bearing a ligand reactive to the same or different type of microorganism to be detected. It would, however, be within the scope of the invention to detect the bead by magnetism, by charge, by density difference or in any other suitable manner.

In a further preferred embodiment of the present invention the ligand is selected from the group consisting of antibody, lectin and oligonucleotide. Preferably, at least one of the ligands is a monoclonal antibody. When the particle is a fluorescent particle, the fluorescent markers attached to the at least one ligand have different fluorescent spectra to that of the fluorescent particle.

In a still further preferred embodiment. the analysing of the treated sample is by flow cytometry. the microorganisms being detected by the presence of fluorescence of the labelled ligand or in combination with the size of the particle, or more preferably, fluorescence of both the marker and the particle. With regard to the detection of the size of the particle, this includes either detecting the known size of the particle or detecting or measuring for an increased size caused by the binding of microorganisms to the particle.

In a still further preferred embodiment of the present invention, the particle is labelled with several ligands reactive to the same or different microorganisms. Furthermore, several different particles can also be used having the same or different ligands bound thereto. For example, in step (b) several different ligands reactive to the same or different microorganisms but provided with different fluorescent markers are utilised to allow the possible detection of more than one type of microorganism bound to the particle.

The method according to the present invention preferably uses one or more fluorescent markers that are excited at 488 nm and emit at wavelengths ranging from green to infra-red. It will be appreciated by one skilled in the art that fluorescent markers that are excited at other wavelengths are also suitable for the present invention.

The present invention is suitable for detecting multiple forms of the same species of microorganism or detecting several different microorganisms from the same sample. The microorganisms bound to the particle may be further treated or analysed after being detected by the method of the present invention.

The number of particles used in the present methods will depend on the type of particle, the type of sample being tested, and the number and type of microorganisms in the sample. It will be appreciated that the microorganism must come in contact with a particle to allow binding. Therefore, the number of particles should be in excess to the number microorganisms in a given sample to ensure detection of the microorganisms of interest. In order to assist in this regard usually at least $10^3$ particles per ml, preferably between $10^4$ to $10^7$ particles per ml are used. When a sample has a lot of particulate material present then usually a higher number of detectable particles is used in order to increase the possibility that the microorganisms present in the sample will come into contact with the particles and bind. The present invention has the advantage that the number of microorganisms in a sample can also be estimated by adding a known number of detectable particles to the sample and counting all of those particles to determine the number that have bound microorganisms. Furthermore, by adding a known number of particles to the sample it is also possible to confirm that the sample was correctly analysed by enumerating the number of particles detected.

In order that the nature of the present invention may be more clearly understood, preferred forms thereof will be described with reference to the following examples and drawings.

MODES FOR CARRYING OUT THE INVENTION

MATERIALS AND METHODS

Coating Beads with Antibody

Figure 1:
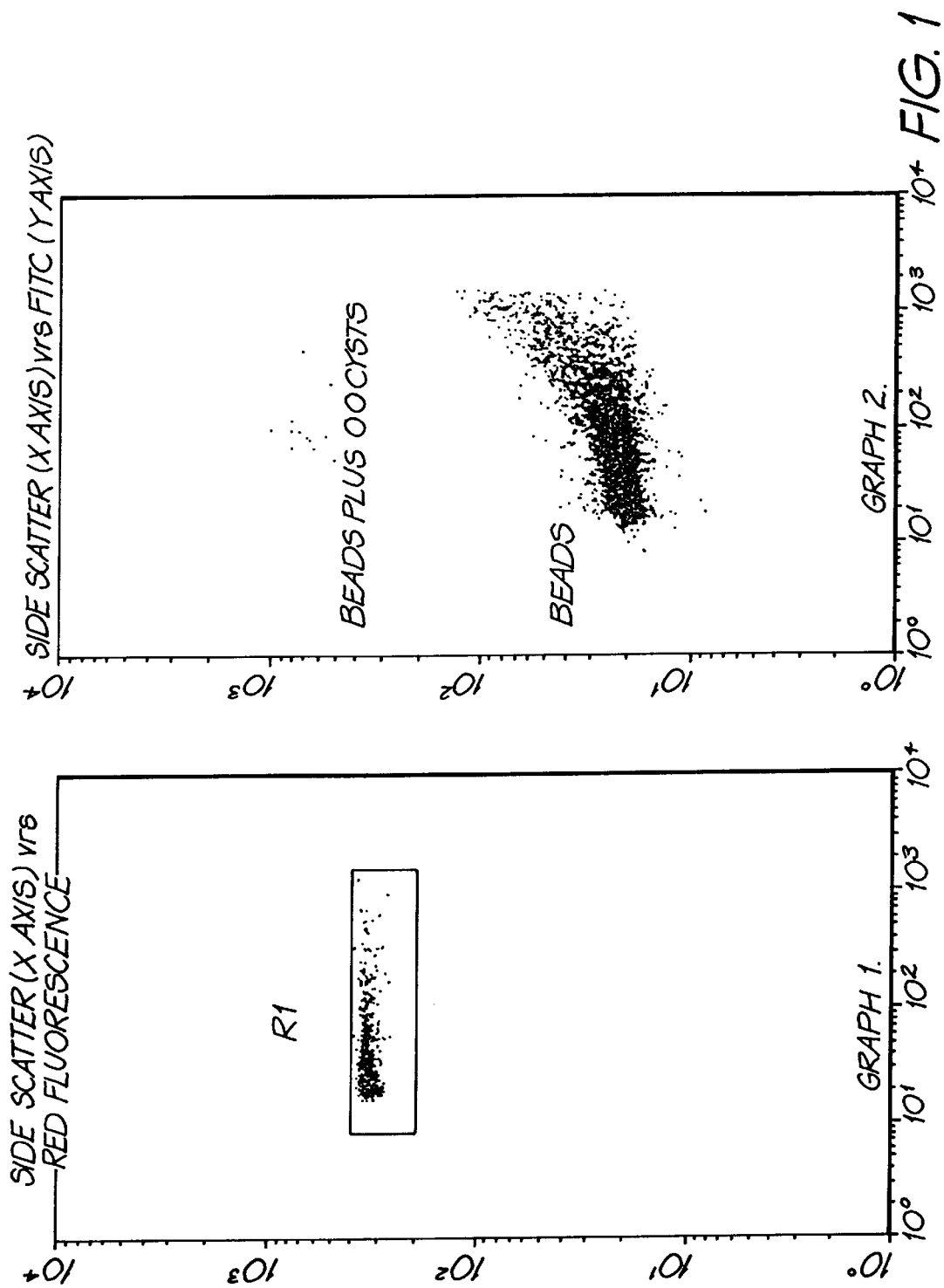
FIG. 1 shows flow cytometry scatter plots representing Cryptosporidium oocysts captured onto fluorescent beads and then bound with a FITC-conjugated Cryptosporidium-specific antibody.

TransFluorSphere 488/685 latex beads were coated as recommended by Molecular Probes (Eugene, USA) with antibody specific to the microorganism of interest.

Antibody (2 mg) specific to either Cryptosporidium (Biox, Sydney), Adenovirus (Silenus, Melbourne) or *Salmonella typhimurium* (Wellcome Diagnostics) was dissolved in 1 ml of 50 mM Tris buffer (pH 8.4) and then dialysed overnight at 4° C. against 50 mM MES buffer (pH 6.0). The antibody was then mixed with 5 ml of 0.2% (w/v) 1μm latex beads (TransFluorSphere 488/685. Molecular Probes. Eugene USA) and incubated at room temperature for 15 min before the addition of 1-ethyl-3(3-dimethylaminopropyl)-carbodiimide (40 mg). The pH was then adjusted to 6.5 by the addition of 0.1 M NaOH. After incubation at room temperature for 2 hours, glycine was added to give a final concentration of 100 mM and the sample incubated for a further 30 min. The beads were then pelleted by centrifuging (13000 g for 2 mil) and the pellet resuspended in 1% (w/v) bovine serum albumin (BSA) in phosphate buffered saline (pH 7.2). The washing procedure was repeated three times before the addition of 0.1%(w/v) sodium azide. The final sample volume was 4 ml. Beads were sonicated for 30 min prior to use.

Using Beads to Label *Cryptosporidium* oocysts in Water Samples

River water samples were concentrated by calcium flocculation (Vesey et al. 1993). Portions (1 ml) of the concentrate were seeded with approximately 1.000 oocysts. BSA was added to a concentration of 1% (w/v) prior to the addition of 20 μl of the crypto-antibody-coated bead suspension. Samples were then incubated at room temperature on a rotary mixer for 30 min.

Oocysts were then labelled with a second fluorochrome. Monoclonal antibody, specific to *Cryptosporidium oocysts* walls, conjugated with fluorescein isothiocyanate (Cellabs Pty Ltd, Sydney, Australia) was added (0.5 ml) and the samples incubated at 37° C. for 20 min.

Using Beads to Label Salmonella

*Salmonella typhimurium* was cultured on MacConkey agar, fixed in 5% (v/v) formalin for 15 min and washed by centrifuging (13000 g for 10 min) and resuspending in PBS. An aliquot (100 μl) containing approximately $1 \times 10^6$ cells was mixed with 20 μl of bead suspension (coated with Salmonella antibody) and then incubated on a rotary shaker for 30 min a room temperature. Salmonella cells attached to beads were labelled with a second fluorochrome by incubating with rabbit anti-Salmonella antibody (Wellcome Diagnostics), washing by centrifuging at 13000 g for 30 seconds. resuspending in a goat anti-rabbit 7-amino-4-methylcoumarin-3-acetic acid (AMCA) (Dako, Glustop, Denmark) conjugated antibody and incubating for 10 min at 37° C. Samples were examined using epifluorescence microscopy. Samples were analysed immediately.

Using Beads to Label Adenovirus

Adenovirus was cultured in human epithelial cells, harvested by freeze thawing the cells and then purified from cell debris by centrifuging (13000 g for 2 min) and retaining the supernatant. The supernatant was then mixed with 20 μl of the bead suspension (coated with Adenovirus antibody) and then incubated on a rotary shaker for 30 min at room temperature. Adenovirus attached to beads were labelled with a second fluorochrome by incubating with the same Adenovirus antibody conjugated with FITC for 20 min at 37° C.

Sample Analysis

Figure 2:
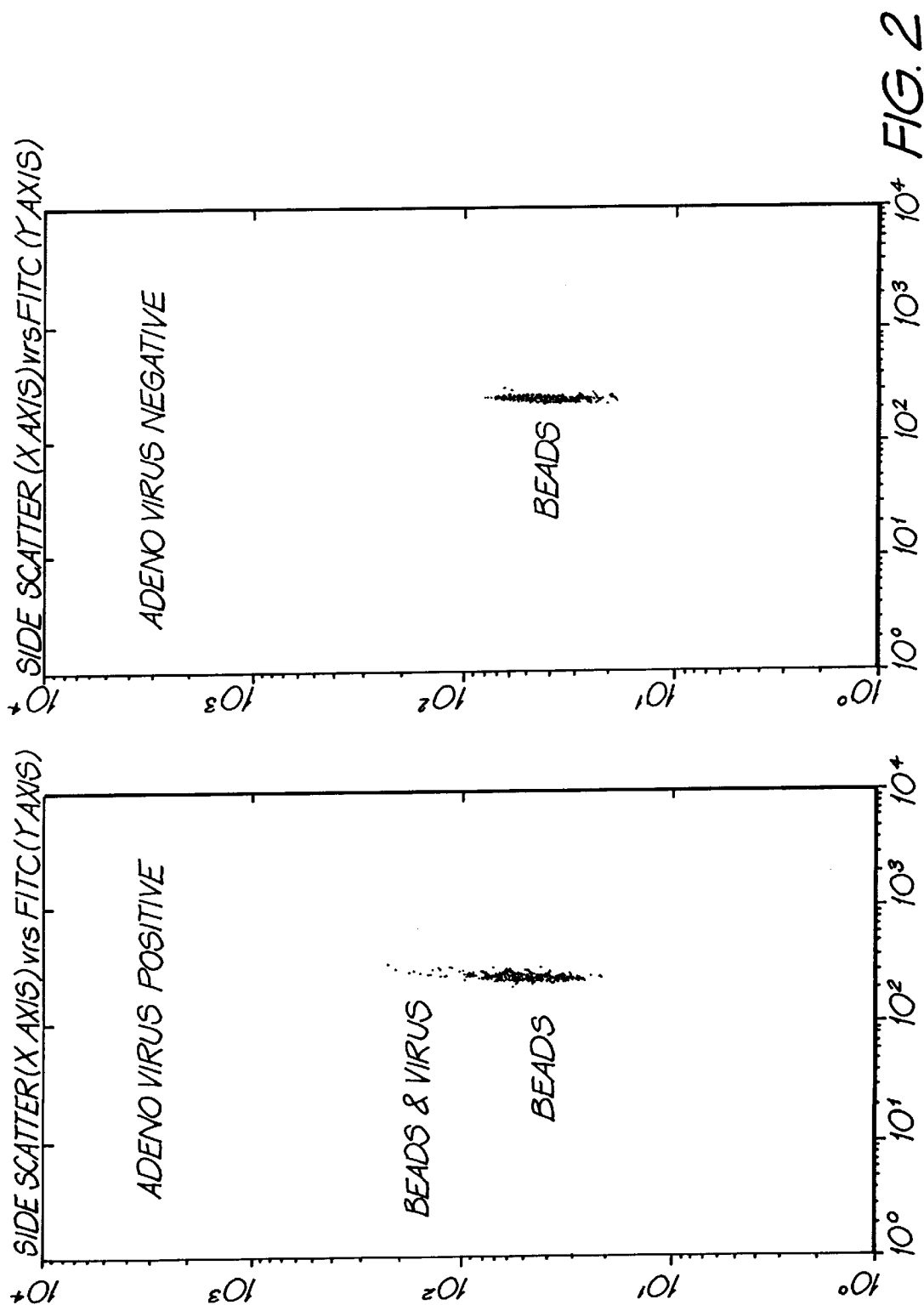
FIG. 2 shows flow cytometry scatter plots representing Adenovirus captured onto fluorescent beads and then bound with FITC-conjugated Adenovirus-specific antibody.

Samples were analysed using a Becton Dickinson Facscan flow cytometer. The discriminator was set on red fluorescence (FL4) at a level slightly less than the fluorescence of the beads. A region (R1) on a scatter plot of green fluorescence (FL1) verses side scatter (graph 1) was defined which enclosed the FITC-labelled oocysts. This region was then used to gate a scatter plot of red fluorescence verses side scatter (graph 2). A region was defined on this second scatter plot which enclosed oocysts attached to beads. The same process was also used for analysis of Adenovirus (FIG. 2).

Colour compensation was performed to separate the fluorescence of the beads from the fluorescence of the labelled organism. Red fluorescence was progressively subtracted from green fluorescence until a second population appeared on the green fluorescence verses side scatter graph.

RESULTS

Cryptosporidium

Analysis of the Cryptosporidium sample by flow cytometry resulted in a distinct population on graph 1 (FIG. 1). This population represents all beads and was enclosed within a region (R1). Gating a graph of side scatter verses FITC on the region R1 produced the scatter graph 2 (FIG. 1). Two populations are observed on graph 2, a large population with a low green signal (spill over from high level of red fluorescence from the beads) which represent the beads and a smaller population with a high FITC signal which represent beads attached to FITC-labelled oocysts.

Adenovirus

Viruses could be detected on the flow cytometer when using the gating and colour compensation procedures that were used for Cryptosporidium. A scatter plot representing a large population of beads with low FITC fluorescence and a small population of beads with high FITC fluorescence (FIG. 2) was observed. This second population represents viruses attached to beads and labelled with FITC. The negative control did not contain any beads with a high FITC signal.

Salmonella

Examination of the beads using epifluorescence microscopy revealed red fluorescing beads attached to blue (AMCA) fluorescing Salmoiiella cells.

The detection of specific or predetermined microorganisms with flow cytometry has the potential to replace existing methodologies for the detection of microorganisins in samples ranging from clinical fluids, water, food and beverages. On way to enable simple and rapid flow cytometric detection of low numbers of microorganisms is to use at least two different coloured fluorochromes for attached to the microorganisms. These fluorochromes are attached to the microorganism via highly specified ligands such as antibodies. This has been achieved previously by conjugating different coloured fluorochromes directly to antibodies (Vesey et al. 1994A).

The present inventors have shown that microorganisms can be detected by flow cytometer by attaching fluorescent beads to the microorganisms. The population representing oocysts attached to beads displayed in graph 2 (FIG. 1) is an identifiable population totally clear from any unassociated coloured bead or interfering noise. The population representing viruses attached to beads in FIG. 2 is also an identifiable population.

The technique of using a fluorescent particle to tag a specific or predetermined microorganism with a fluorescent label has several advantages over using only a fluorochrome-conjugated antibody. Firstly, only a single bead needs to be attached to the microorganism to achieve detectable fluorescence. To achieve the same level detection using only a fluorochrome conjugated antibody requires thousands of antibodies to be attached to the microorganism. These thousands of antibodies cover and mask available antigen sites. If only a single type of antigen is available on the surface of a microorganism, then it is not always possible to label the surface of the organism with a second antibody. The present inventors have found that only one antigen is presented by Cryptosporidium and therefore this organism is difficult to detect by previous methods.

If the microorganism is labelled with an antibody coated fluorescent bead then there are many antigen sites still available on the surface of the organism for attaching an antibody conjugated to a fluorochrome. This technique enables two colour fluorescence labelling of a microorganism with a single antibody as shown by the present inventors.

A further advantage of the fluorescent bead labelling technique is that it enables the use of new fluorescence emission wavelengths. Until recently the number of different colours that can be detected by a single laser flow cytometer has been limited to two. These are a green fluorochrome such as FITC and a red fluorochrome such as PE. A third colour is now possible using tandem fluorochromes such as PE/Texas red where the PE pumps the Texas red. These tandem fluorochromes however are not bright enough for many applications. When attempting to detect microorganisms the fluorescence signals need to be very bright. The fluorescent beads enable the use of a third and even a fourth very bright fluorescent signal. This is because beads with a range of different fluorescent emissions are available. Beads with emissions as far into the infrared as 720 nm are available.

Examples of fluorescent beads and their production that are suitable for use in the present invention can be found in U.S. Pat. No. 5,326,692.

The use of fluorescent beads as a label improves flow cytometric detection. This is because the beads can be used as the size or fluorescence discriminator. The cytometer can be set so that it ignores all other particles except for the beads. This overcomes coincidence problems due to the sample containing more particles than the cytometer can examine. It also means that a known number of particles need to be examined for all samples.

The bead technology is highly applicable to the detection of bacteria. It enables multiple bright fluorescence signals to be achieved on the surface of a range of bacteria. The production of antibodies to large groups of bacteria (eg all gram negative bacteria) and then coating beads with these antibodies will allow the use of a single reagent for a range of microorganisms or their sub-types.

The application where this bead technology will have the most benefits will be the flow cytometric detection of very small particles such as viruses. Coating beads with virus specific antibodies and reacting with samples captures viruses onto the beads. The virus is then labelled with a second fluorochrome enabling detection. This is the first, simple virus detection procedure that can be performed within minutes.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Vesey. G., Narai. J., Ashbolt. N., Williams. K. L. and Veal. D. 1994A. Detection of specific microorganisms in environmental samples using flow cytometry, p.489–522. *In Methods in Cell Biology-Flow Cytometry Second Edition*. Academic Press Inc., New York.

Vesey. G., Hutton. P. E., Champion. A. C., Ashbolt. N. J., Williams. K. L., Warton. A. and Veal. D. A. 1994B. Application of flow cytometric methods for the routine detection of Cryptosporidium and Giardia in water. Cytometry, 16: 1–6.

Vesey. G., Slade, J. S., Byrne. M., Shepherd, K., and Fricker. C. R., 1993. A new method for the concentration of *Cryptosporidium oocysts* from water. *J. Appl. Bact.* 75.82–86.

What is claimed is:

1. A method of detecting the presence and estimating the number of microorganisms of a predetermined type in a sample containing the microorganisms, the method comprising the steps of:

(a) treating the sample with a detectable fluorescent particle, the fluorescent particle comprising an antibody which binds to the microorganisms of the predetermined type, the sample being treated for a period of time sufficient to allow the microorganisms of the predetermined type in the sample to bind to the fluorescent particle via the antibody;

(b) further treating the sample with an antibody labeled with a fluorescent marker having a different fluorescent spectrum to that of the fluorescent particle, the antibody being the antibody as used in step (a) which is capable of binding to the microorganisms of the predetermined type, the sample being treated for a period of time sufficient to allow the antibody to bind to the microorganisms of the predetermined type;

(c) analyzing the sample by flow cytometry so as to detect the presence of a fluorescent particle in combination with a fluorescent marker, wherein such a combination with a fluorescent marker is indicative of the presence of microorganisms of the predetermined type in the sample; and (d) estimating the number of microorganisms of the predetermined type in the sample by measuring the intensity of the fluorescence of the fluorescent marker in combination with the fluorescent particle.

2. The method according to claim 1 wherein the fluorescent particle is a fluorescent latex bead.

3. The method according to claim 2 wherein the fluorescent latex bead has a diameter from 10 nanometers to 0.1 millimeters.

4. The method according to claim 1 wherein the sample is treated with at least $10^3$ detectable fluorescent particles per milliliter sample.

5. The method according to claim 4 wherein the sample is treated with between $10^4$ and $10^7$ detectable fluorescent particles per milliliter sample.

6. The method according to claim 1 wherein the microorganisms are selected from the group consisting of protozoa, bacteria, fungi and viruses.

7. The method of claim 6 wherein the microorganisms are viruses.

8. The method according to claim 1 wherein the antibody is a monoclonal antibody.

9. The method according to claim 1 wherein the fluorescent marker is excited at 488 nm and emits at wavelengths ranging from green to infra-red.

10. The method according to claim 1 wherein the microorganisms are detected by the presence of fluorescence of the labeled antibody, by fluorescence of the labeled antibody in combination with the size of the fluorescent particle, or by fluorescence of both the antibody and the fluorescent particle.

11. The method according to claim 1 wherein the fluorescent particle comprises at least two different antibodies.

12. The method according to claim 1 wherein step (b) further comprises at least two different antibodies, each different antibody being labeled with a different fluorescent marker having a different fluorescence spectrum to that of the fluorescent particle and the other labeled antibodies.

13. The method according to claim 1 wherein the detectable fluorescent particle comprises at least two different antibodies, each antibody capable of binding to a different predetermined type of microorganism, step (b) further comprises at least two different antibodies as in step (a), each different antibody being labelled with a different fluorescent marker, having a different fluorescence spectrum to that of the fluorescent particle and the other labeled antibodies, and being capable of binding to a different type of microorganism so as to allow detection of at least two types of microorganisms in the sample by analyzing for the presence of at least two different fluorescent-labeled antibodies in combination with the fluorescent particle.

14. The method according to claim 1 wherein the number of microorganisms of a predetermined type in the sample is estimated by adding to the sample a known number of detectible fluorescent particles and analyzing the fluorescent particles in the sample for combination with one or more of the fluorescent markers and estimating the number of microorganisms in the sample from the number of detectible fluorescent particles associated with the fluorescent markers.

* * * * *